(12) United States Patent
Sharma (10) Patent No.: US 10,884,087 B2
(45) Date of Patent: Jan. 5, 2021

(54) APPARATUSES AND METHODS TO IMPROVE CHEMICAL SPECIES SEPARATION IN MAGNETIC RESONANCE IMAGING

(71) Applicant: CANON MEDICAL SYSTEMS CORPORATION, Otawara (JP)

(72) Inventor: Samir Dev Sharma, Solon, OH (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/290,574

(22) Filed: Mar. 1, 2019

(65) Prior Publication Data
US 2020/0278406 A1 Sep. 3, 2020

(51) Int. Cl.
| | |
|---|---|
| G01R 33/48 | (2006.01) |
| G01R 33/485 | (2006.01) |
| G01R 33/561 | (2006.01) |
| G01R 33/565 | (2006.01) |
| G16H 30/40 | (2018.01) |
| G06T 7/00 | (2017.01) |

(Continued)

(52) U.S. Cl.
CPC ....... *G01R 33/4828* (2013.01); *G01R 33/485* (2013.01); *G01R 33/5615* (2013.01); *G01R 33/56527* (2013.01); *G01R 33/24* (2013.01); *G01R 33/50* (2013.01); *G06T 7/0012* (2013.01); *G06T 2207/10088* (2013.01); *G06T 2207/30004* (2013.01); *G16H 30/40* (2018.01)

(58) Field of Classification Search
CPC .............. G01R 33/4828; G01R 33/485; G01R 33/56527; G01R 33/5615; G01R 33/50; G01R 33/24; G06T 7/0012; G06T 2207/10088; G06T 2207/30004; G16H 30/40

See application file for complete search history.

(56) References Cited

U.S. PATENT DOCUMENTS

| | | |
|---|---|---|
| 4,720,679 A | 1/1988 | Patrick et al. |
| 2013/0208969 A1 | 8/2013 | Bashir et al. |

(Continued)

OTHER PUBLICATIONS

Diego Hernando, et al., "Robust Water/Fat Separation in the Presence of Large Field Inhomogeneities Using a Graph Cut Algorithm", Magnetic Resonance in Medicine 63, 2010.

(Continued)

*Primary Examiner* — Susan S Lee
(74) *Attorney, Agent, or Firm* — Oblon, McClelland, Maier & Neustadt, L.L.P.

(57) ABSTRACT

A method and apparatuses are provided to perform chemical species separation in magnetic resonance (MR) imaging (MRI). At least three MR images corresponding respectively to different echo times are obtained and represent signals from multiple chemical species including a first species and a second species in a tissue. A plurality of dual-echo pairs is selected from the at least three MR images. For each pair, a set of dual-echo separated images including a B0 field map, a first image for the first species, and a second image for the second species is estimated. An initial set of combined images including at least one of: an initial combined B0 field map, first, and second image is generated by combining at least one of: two or more of the B0 field maps, two or more of the first images, and two or more of the second images.

20 Claims, 8 Drawing Sheets

(51) Int. Cl.
*G01R 33/24* (2006.01)
*G01R 33/50* (2006.01)

(56) References Cited

U.S. PATENT DOCUMENTS

| 2014/0126795 | A1 | 5/2014 | Zhong et al. | |
|---|---|---|---|---|
| 2016/0187447 | A1 | 6/2016 | Hwang et al. | |
| 2017/0038446 | A1* | 2/2017 | Liu | A61B 5/055 |
| 2017/0234957 | A1* | 8/2017 | Zho | G01R 33/443 |
| | | | | 324/309 |

OTHER PUBLICATIONS

Wenmiao Lu, et al., "Multiresolution Field Map Estimation Using Golden Section Search for Water-Fat Separation", Magnetic Resonance in Medicine 60, 2008.

Romu T., et al., "Robust water fat separated dual-echo MRI by phase-sensitive reconstruction", Megn Reson Med., 78(3), Sep. 2017.

Tao Zhang, et al., "Resolving Phase Ambiguity in Dual-Echo Dixon Imaging Using a Projected Power Method", Magn Reson Med., 77(5), May 2017.

Jeffrey Tsao, et al., "Hierarchical IDEAL: Fast, Robust, and Multiresolution Separation of Multiple Chemical Species from Multiple Echo Times", Magnetic Resonance in Medicine 70, 2013.

Huanzhou Yu, et al., "Field Map Estimation with a Region Growing Scheme for Iterative 3-Point Water-Fat Decomposition", Magnetic Resonance in Medicine 54, 2005.

Xiaodong Zhong, et al., "Liver Fat Quantification Using a Multi-Step Adaptive Fitting Approach with Multi-Echo GRE Imaging", Magnetic Resonance in Medicine 72, 2014.

Johan Berglund, et al., "Two-point Dixon Method With Flexible Echo Times", Magnetic Resonance in Medicine 65, 2011.

Holger Eggers, et al., "Dual-Echo Dixon Imaging with Flexible Choice of Echo Times", Magnetic Resonance in Medicine 65, 2011.

\* cited by examiner

CONFIDENCE MAP 295E

| C(1,1)=2/3 | C(1,2)=2/3 | C(1,3)=1 | C(1,4)=1 |
|---|---|---|---|
| C(2,1)=2/3 | C(2,2)=1 | C(2,3)=2/3 | C(2,4)=1 |
| C(3,1)=1 | C(3,2)=2/3 | C(3,3)=1 | C(3,4)=1 |

CONFIDENCE MAP 295E'

| C(1,1)=2/3 | C(1,2)=2/3 | C(1,3)=1 | C(1,4)=1 |
|---|---|---|---|
| C(2,1)=2/3 | C(2,2)=1 | C(2,3)=1 | C(2,4)=1 |
| C(3,1)=1 | C(3,2)=2/3 | C(3,3)=1 | C(3,4)=1 |

APPARATUSES AND METHODS TO IMPROVE CHEMICAL SPECIES SEPARATION IN MAGNETIC RESONANCE IMAGING

TECHNICAL FIELD

This disclosure relates to improving image quality in reconstructed Magnetic resonance imaging (MRI) images.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

MRI systems and methods are widely used, particularly for medical imaging and diagnosis. MRI systems generally create images through a subject's body. The images can include signals from multiple chemical species in the subject's body. It is desirable to separate the signals from the multiple chemical species, for example, for better disease diagnosis.

BRIEF DESCRIPTION OF THE DRAWINGS

A more complete understanding of this disclosure is provided by reference to the following detailed description when considered in connection with the accompanying drawings, wherein.

DETAILED DESCRIPTION

Exemplary embodiments are illustrated in the referenced figures of the drawings. It is intended that the embodiments and figures disclosed herein are to be considered illustrative rather than restrictive. No limitation on the scope of the technology and of the claims that follow is to be imputed to the examples shown in the drawings and discussed herein.

The embodiments are mainly described in terms of particular processes and systems provided in particular implementations. However, the processes and systems will operate effectively in other implementations. Phrases such as 'an implementation', 'an embodiment', 'one embodiment', and 'another embodiment' can refer to the same or different embodiments. The embodiments/implementations will be described with respect to methods and compositions having certain components. However, the methods and compositions can include more or less components than those shown, and variations in the arrangement and type of the components can be made without departing from the scope of the present disclosure.

The exemplary embodiments are described in the context of methods having certain steps. However, the methods and compositions operate effectively with additional steps and steps in different orders that are not inconsistent with the exemplary embodiments. Thus, the present disclosure is not intended to be limited to the embodiments shown, but is to be accorded the widest scope consistent with the principles and features described herein and as limited only by the appended claims.

Furthermore, where a range of values is provided, it is to be understood that each intervening value between an upper and lower limit of the range—and any other stated or intervening value in that stated range—is encompassed within the disclosure. Where the stated range includes upper and lower limits, ranges excluding either of those limits are also included. Unless expressly stated, the terms used herein are intended to have the plain and ordinary meaning as understood by those of ordinary skill in the art. Any definitions are intended to aid the reader in understanding the present disclosure, but are not intended to limit the meaning of such terms unless specifically indicated.

The apparatuses and methods described herein achieve several advantages over related methods. These advantages include: improving image quality of medical images, such as images generated by magnetic resonance imaging (MRI). The apparatuses and methods described herein are provided as non-limiting example implementations of the present disclosure. As will be understood by those skilled in the art, the present disclosure may be embodied in other specific forms without departing from the spirit or essential characteristics thereof. Accordingly, the detailed description is intended to be illustrative, but not limiting of the scope of the disclosure. The disclosure, including any readily discernible variants of the teachings herein, defines, in part, the scope of the foregoing claim terminology such that no inventive subject matter is dedicated to the public.

In some embodiments of magnetic resonance (MR) imaging (MRI), at least three MR images can be acquired from a tissue using different echo times. The tissue includes multiple chemical species, including a first chemical species (or a first species), a second chemical species (or a second species). Each of the at least three images can include signals of the multiple chemical species, such as a first signal of the first species, a second signal of the second species. In general, it is desirable to implement chemical species separation that separates the signals of the multiple chemical species so that a first image represents the first signal of the first species, a second image represents the second signal of the second species. The first image can be referred to as a first species only image and the second image can be referred to as a second species only image.

In order to perform chemical species separation, a B0 field map that mainly represents spatial inhomogeneity of magnetic field strength B0 in the tissue is to be estimated. In general, a more accurate estimation of the B0 field map can result in more accurate chemical species separation. According to aspects of the disclosure, a plurality of dual-echo pairs can be selected from the at least three MR images and each of the plurality of dual-echo pairs can be separately processed in order to estimate the B0 field map and separate the multiple chemical species. As described below, employing the plurality of dual-echo pairs instead of a single dual-echo pair and separately processing the plurality of dual-echo pairs instead of jointly processing the at least three MR images can enable a more accurate estimation of the B0 field map and thus a more accurate separation of the multiple chemical species.

Figure 1A:
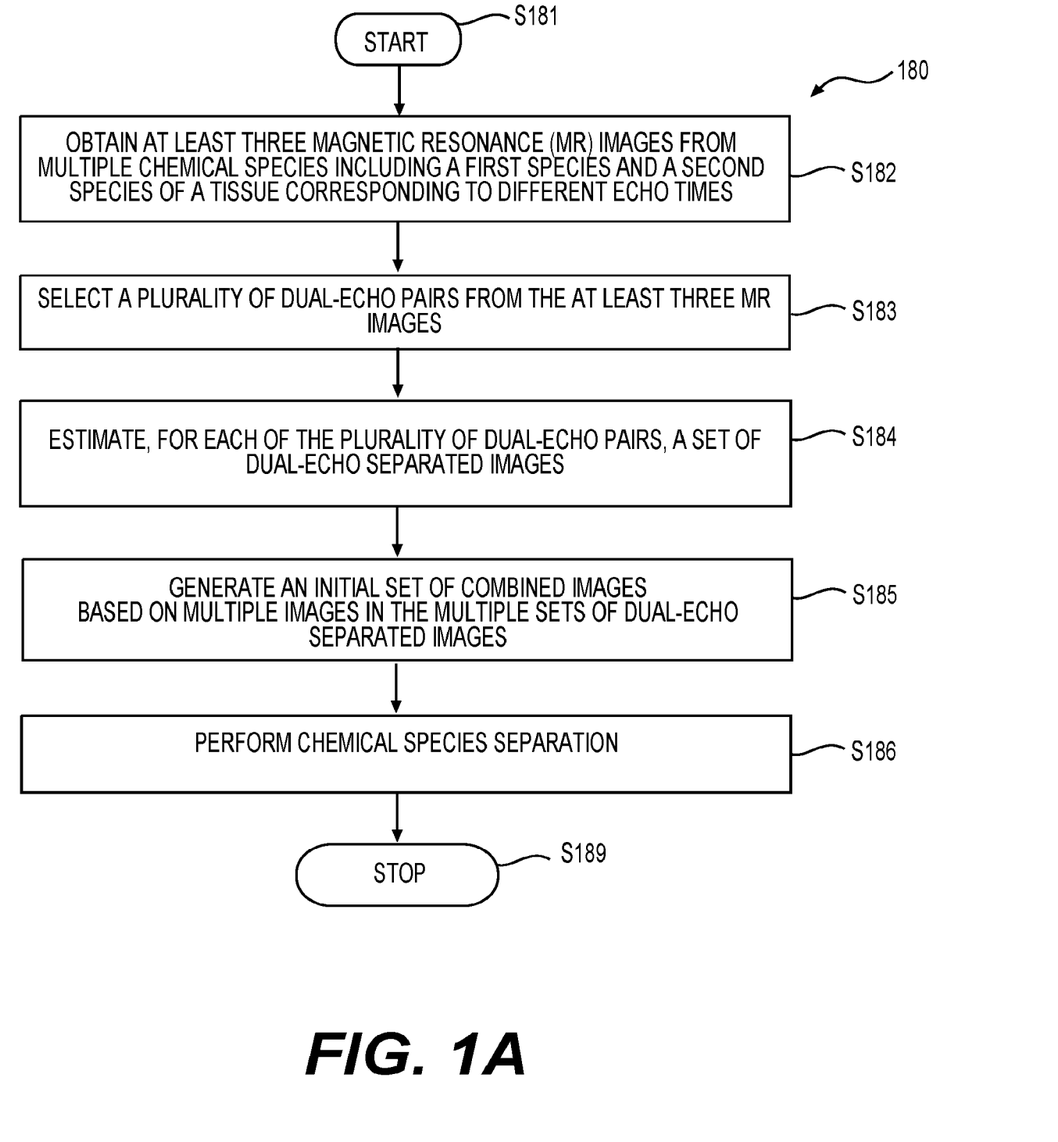
FIG. 1A shows an example of a method 180 to perform chemical species separation according to an embodiment of the disclosure.
Figure 1B:
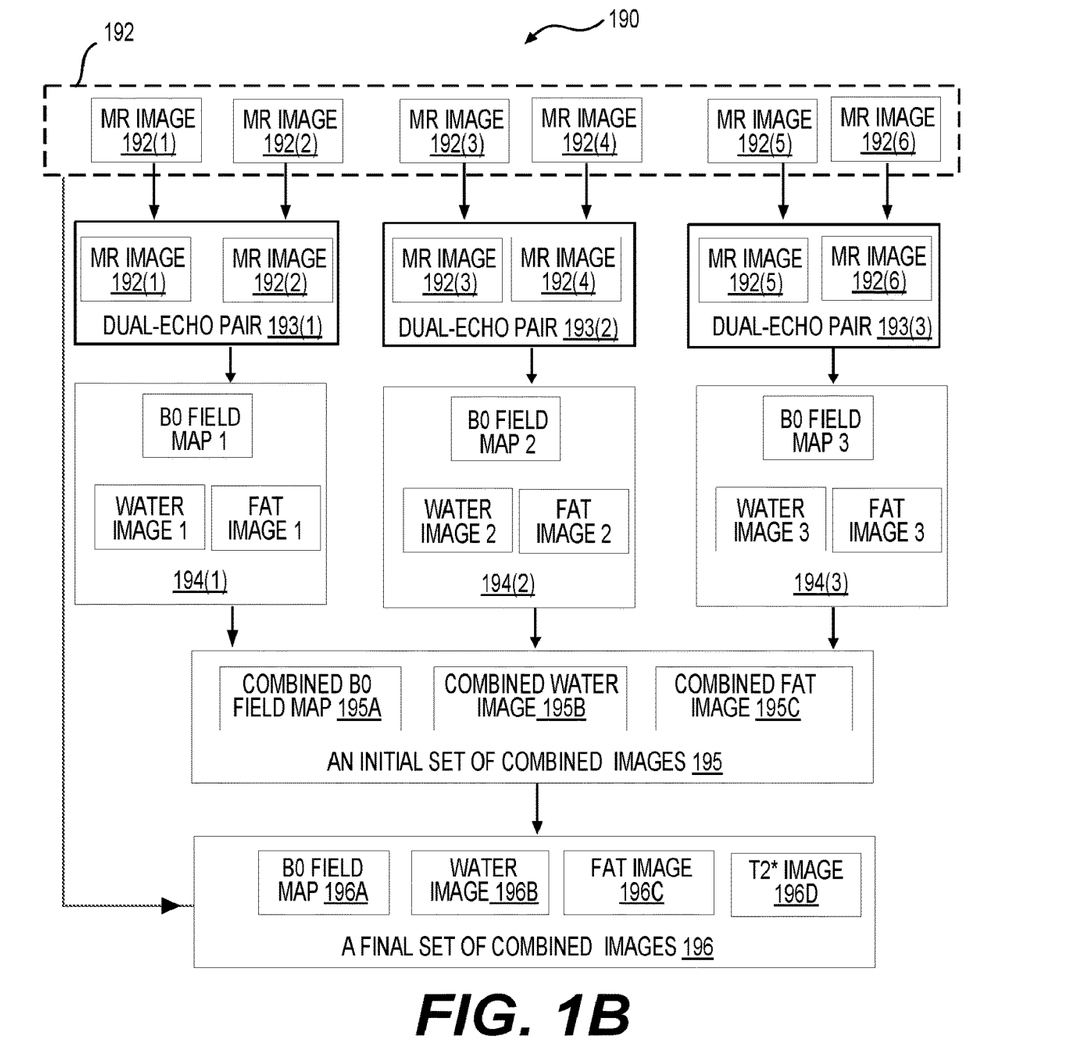
FIG. 1B shows an example 190 corresponding to the method 180 according to an embodiment of the disclosure.

Referring now to the drawings, where like reference numerals designate identical or corresponding parts in different figures, FIG. 1A shows an example of a method 180 to perform chemical species separation according to an embodiment of the disclosure. FIG. 1B shows an example 190 corresponding to the method 180 according to an embodiment of the disclosure. The method 180 starts at S181, and proceeds to S182.

At S182, at least three MR images corresponding to different echo times (TEs) are obtained from a tissue. Similar to the above description, the tissue has multiple chemical species including a first species, a second species, and the like. Each of the at least three MR images represents signals from the multiple chemical species, and the signals includes a first signal of the first species, a second signal of the second species, and the like.

In various examples of MRI, such as the example 190 in FIG. 1B, water and fat are major contributors to the signals where the first species is water and the second species is fat. Thus, the first signal is a water signal and the second signal is a fat signal. The fat signal (or a fat presence) can hinder assessment of a MR image, such as lesions or cancerous regions in the MR image that includes both the water signal and the fat signal. Therefore, it is advantageous to separate the multiple chemical species, such as water and fat. In an example, a chemical species encoded (CSE) imaging based on one or more frequency shifts can be used in chemical species separation. A frequency shift refers to a difference in resonance frequencies (or Larmor frequencies) of two chemical species, and reflects magnetic characteristics of the two chemical species. For example, the frequency shift between fat and water at 1.5 Tesla (T) is about 220 Hertz (Hz) or 3.5 parts per million (ppm) with respect to the Larmor frequency of water at 1.5 T. When multiple MR images are acquired with different echo times, the contrast of the water signal and the fat signal in the multiple MR images is altered due to the frequency shift between water and fat, and thus, the water signal and the fat signal can be separated in post-processing of the multiple MR images.

In the FIG. 1A example, the number of MR images in the at least three MR images can be any suitable integer larger than 2, (e.g., 3, 4, 5, or 6). The at least three MR images are acquired at the different echo times (TEs), such as a first echo time TE1, a second echo time TE2, a third echo time TE3, and the like in an ascending order and corresponding to a MRI pulse sequence. The different TEs can be specified with respect to a time t0 of 0 milliseconds (ms) where the time t0 is a time of excitation of a MRI pulse sequence, for example, a gradient-recalled echo. The different echo times can be any suitable times. In an example, time differences between adjacent echo times can be 1 ms to a few ms. The at least three MR images can be, e.g., three-dimensional (3D) images, two-dimensional (2D) images. A pixel in a 3D image is also referred to as a voxel (i.e., volume pixel) that covers a unit volume of the tissue while a pixel in a 2D image covers a unit area of the tissue.

Figure 3:
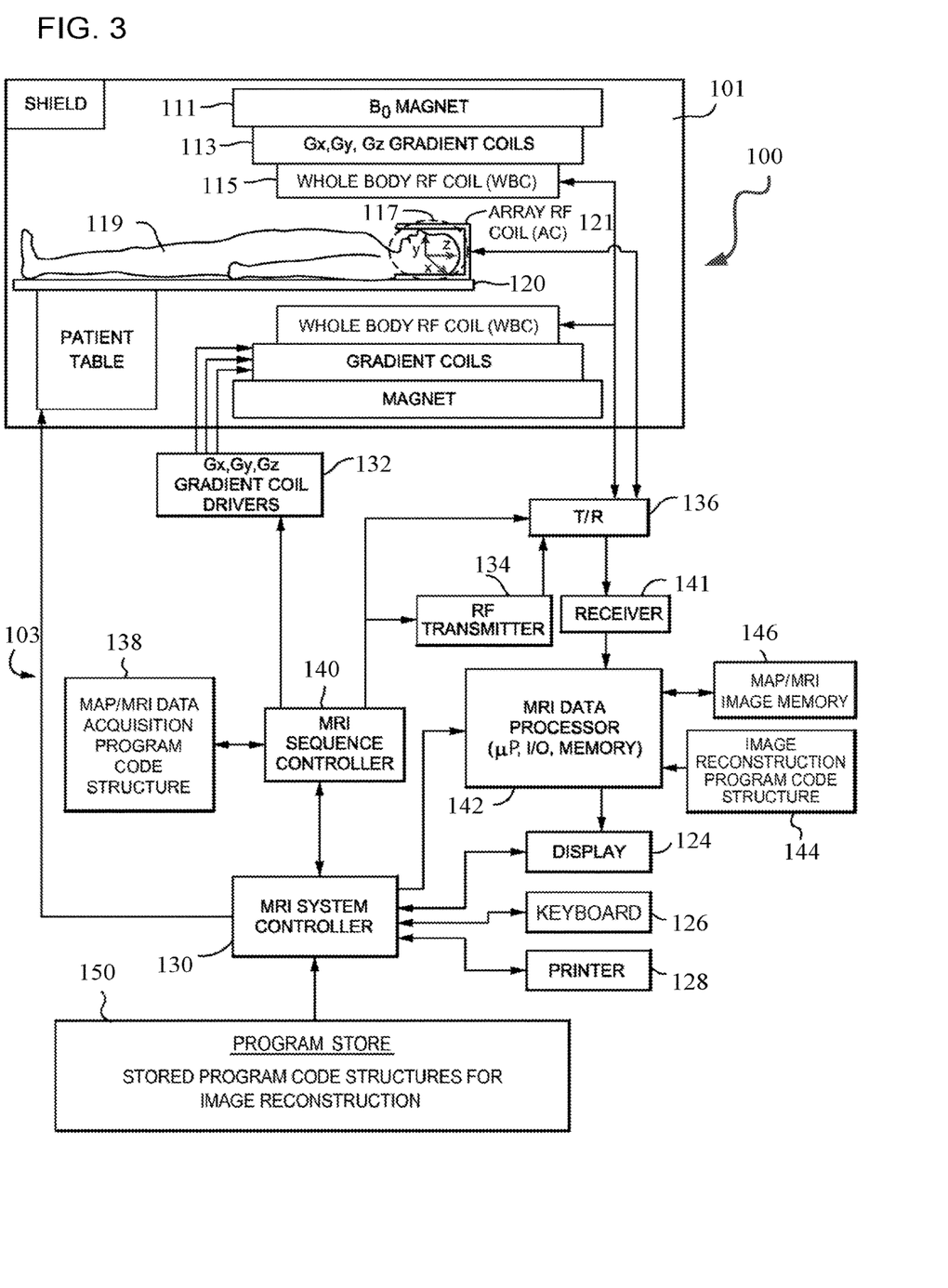
FIG. 3 shows a non-limiting example of a magnetic resonance imaging (MRI) system 100 according to an embodiment of the disclosure.

Referring to FIG. 1B, the at least three MR images 192 in the example 190 can be acquired using a MRI system shown in FIG. 3. The at least three MR images 192 includes six MR images 192(1)-(6) acquired at six different TEs, TE1 to TE6, respectively. The tissue includes water and fat. Each of the six MR images 192(1)-(6) includes the water signal and the fat signal to be separated.

At S183, a plurality of dual-echo pairs can be selected from the at least three MR images. The plurality of dual-echo pairs can include any suitable combination of the at least three MR images, and one of the plurality of dual-echo pairs is different from another of the plurality of dual-echo pairs. Each of the at least three MR images can appear in any suitable number, such as 0, 1, 2, or the like, of the plurality of dual-echo pairs.

Referring to the example 190 in FIG. 1B, the plurality of dual-echo pairs includes three dual-echo pairs 193(1)-(3). The dual-echo pair 193(1) includes the MR images 192(1)-(2), the dual-echo pair 193(2) includes the MR images 192(3)-(4), and the dual-echo pair 193(3) includes the MR images 192(5)-(6).

In another example, the plurality of dual-echo pairs includes five dual-echo pairs, such as a dual-echo pair of the MR images 192(1)-(2), a dual-echo pair of the MR images 192(2)-(3), a dual-echo pair of the MR images 192(3)-(4), a dual-echo pair of the MR images 192(4)-(5), and a dual-echo pair of the MR images 192(5)-(6).

In a third example, the plurality of dual-echo pairs includes three dual-echo pairs, such as a dual-echo pair of the MR images 192(1) and 192(3), a dual-echo pair of the MR images 192(2) and 192(4), and a dual-echo pair of the MR images 192(3) and 192(5).

The plurality of dual-echo pairs can include any suitable number of dual-echo pairs and the number is larger than 1. For example, the number of dual-echo pairs can be an odd number, such as 3, 5, or the like, to facilitate a voting method as described below. A time difference between the two echo times of one of the plurality of dual-echo pairs can be any suitable duration. In an example, the time difference is restrained to be less than a limit, such as a few ms.

At S184, for each pair of the plurality of dual-echo pairs, a set of images (or a set of dual-echo separated images) is estimated and the signals of the multiple chemical species are separated in the set of images. The set of images can include a first image representing the first signal of the first species. The set of images can also include a second image representing the second signal of the second species, a B0 field map mainly representing spatial inhomogeneity of magnetic field strength, and/or the like. Any suitable chemical species separation method can be used to obtain the set of images based on the corresponding dual-echo pair.

Referring to the example 190 in FIG. 1B, for the dual-echo pair 193(i), the set of images 194(i) can include a B0 field map i, a water image i, and a fat image i, where i is an integer and 1≤i≤3. For purposes of clarity, the descriptions below are given for obtaining the set of images 194(1) based on the dual-echo pair 193(1) that includes the MR images 192(1)-(2). In an embodiment, the MR images 192(1)-(2) are complex images. Thus, values of a pair of pixels at a same location of the tissue in the MR images 192(1)-(2) are two complex values $S_1$ and $S_2$, respectively. That is, for a given pixel location $S_1$ is the complex value for the pixel in MR image 192(1), and $S_2$ is the complex value for the pixel in MR image 192(2). The two complex values $S_1$ and $S_2$ can be related to four parameters $W_0$, $F_0$, $\varphi 1$, and $\Delta\varphi$ by Eqs. (1)-(2) as below.

$$S_1 = f_1(W_0, F_0, e^{i\varphi 1}) \quad (1)$$

$$S_2 = f_2(W_0, F_0, e^{i\varphi 1}, e^{i\Delta\varphi}) \quad (2)$$

In Eqs. (1)-(2), the four parameters are real-valued and include: the water signal at t0, $W_0$, the fat signal at t0, $F_0$, a phase $\varphi 1$ representing a phase of the water signal at TE1, and a difference phase $\Delta\varphi$ representing a phase accumulation during a time difference $\Delta TE=TE2-TE1$. That is, $\Delta TE$ is the time difference between the second echo time TE2 and the first echo time TE1. The difference phase $\Delta\varphi$ is mostly due to the spatial inhomogeneity of the magnetic field strength B0, and a map of the difference phase $\Delta\varphi$ is referred to as the B0 field map. The function $f_1$ depicts a first relationship between the complex value $S_1$ and 3 of the four parameters, $W_0$, $F_0$, and $\varphi 1$. The function $f_2$ depicts a second relationship between the complex value $S_2$ and the four parameters, $W_0$, $F_0$, $\varphi 1$, and $\Delta\varphi$. The functions $f_1$ and $f_2$ are known, and the complex values $S_1$ and $S_2$ are known from the MR images 192(1)-(2). Thus, the four parameters $W_0$, $F_0$, $\varphi 1$, and $\Delta\varphi$ can be obtained by solving the Eqs. (1) and (2). In various examples, dual-echo separation techniques can be used to obtain the four parameters by solving the Eqs. (1)-(2). Accordingly, the set of images 194(1) including the B0 field map 1, the water image 1 (or the water-only image 1) of the water signal at t0, $W_0$, and the fat image 1 (or the fat-only image 1) of the fat signal at t0, $F_0$, can be obtained.

In some examples, other relationship(s) different from that described by Eqs. (1)-(2) can relate the complex values $S_1$ and $S_2$ with one or more of the four parameters, and thus, the water signal and the fat signal can also be separated based on the other relationship(s).

In some examples, other than the water signal at t0, $W_0$ and the fat signal at t0, $F_0$, the water signal and the fat signal at a different echo time can be used in the water image 1 and the fat image 1, respectively.

Similarly, the above described method can be suitably adapted to the dual-echo pair 193(2) to obtain the set of images 194(2) including a B0 field map 2, a water image 2, and a fat image 2. The above described method can be suitably adapted to the dual-echo pair 193(3) to obtain a set of images 194(3) including a B0 field map 3, a water image 3, and a fat image 3. The water signal and the fat signal at a same echo time that is different from t0 can be used in the water images 1-3 and the fat images 1-3, respectively.

At S185, an initial set of combined images is generated based on multiple images in the multiple sets of images for the plurality of dual-echo pairs and the signals of the multiple chemical species are separated in the initial set of combined images. Any suitable multiple images can be used to generate the initial set of combined images, and the multiple images are from at least two different sets of the multiple sets of images for at least two of the plurality of dual-echo pairs. The initial set of combined images can include at least one of: an initial combined first image, an initial combined second, and an initial combined B0 field map. Referring to FIG. 1B, the initial set of combined images 195 can include an initial combined B0 field map 195A, an initial combined water image 195B, and an initial combined fat image 195C. Any suitable methods can be used to generate the initial set of combined images 195 based on any suitable multiple images in the multiple sets of images 194(1)-(3).

Figure 1C:
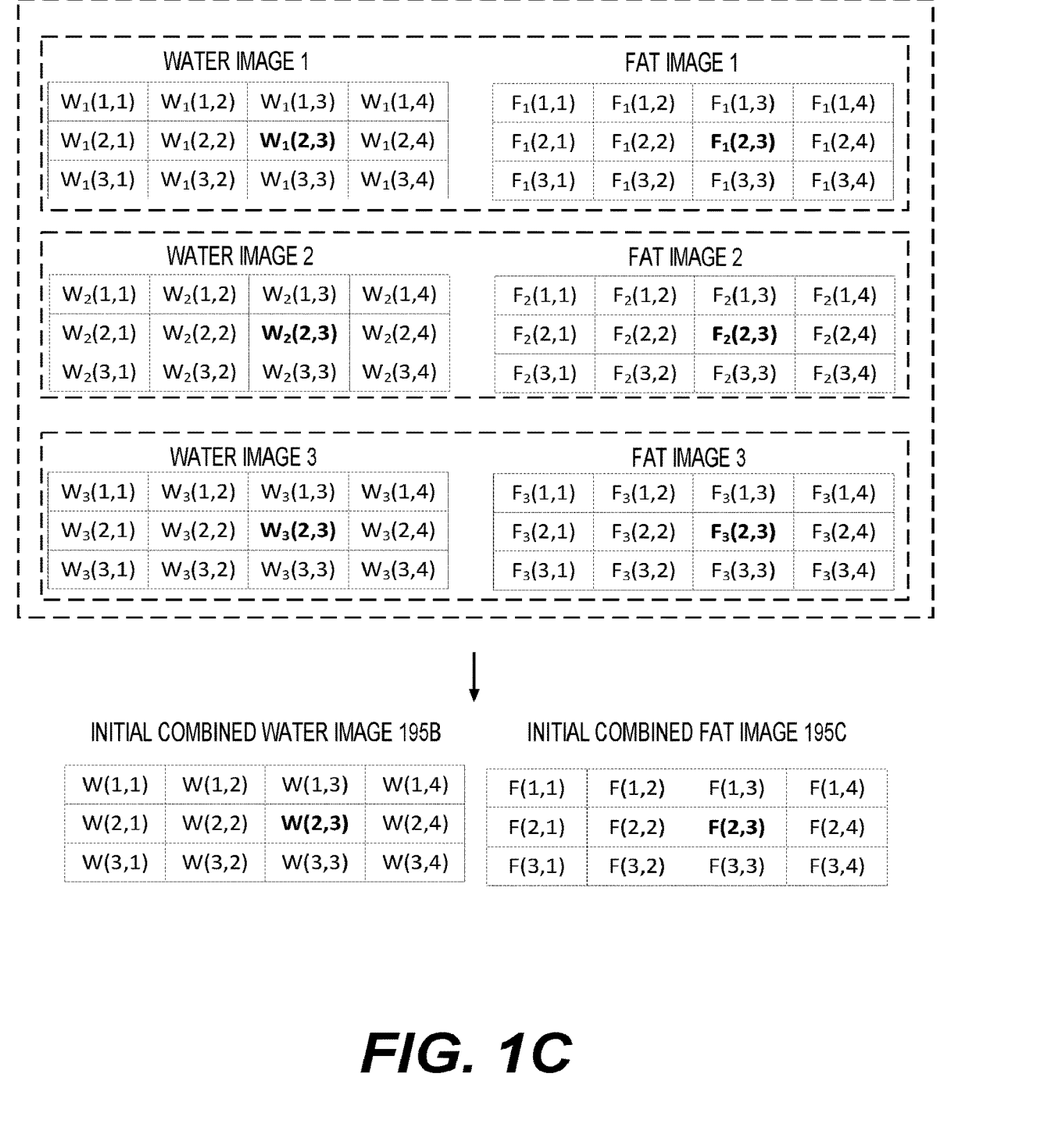
FIG. 1C shows an example to generate an initial set of combined images according to an embodiment of the disclosure.

In an embodiment, the initial set of combined images can be generated by using a voting method based on images obtained from an odd number of the plurality of the dual-echo pairs. FIG. 1C shows an example to generate at least one of the initial set of combined images 195 by using the voting method according to an embodiment of the disclosure. The voting method is based on the water images 1-3 and the fat images 1-3 obtained from the three dual-echo pairs 193(1)-(3). In the example shown in FIG. 1C, the water images 1-3 and the fat images 1-3 are 3×4 2D images, and the initial combined water image 195B is also a 3×4 2D image. The voting method can also be suitably adapted to 3D images or the like. To determine a value of a pixel at a location in the tissue, such as a pixel W(2,3) in the initial combined water image 195B, values of corresponding pixels $W_1(2,3)$, $W_2(2,3)$, and $W_3(2,3)$ at the same location in the water images 1-3 can be used.

In the voting method of FIG. 1C, whether a majority of the pixels is dominated by water or not can be determined. Subsequently, a value of the pixel W(2,3) in the initial combined water image 195B is calculated based on values of the pixels in the majority.

Whether the pixel location (2,3) is considered water-dominant or not for majority of species-image pairs (i.e., $\{W_1,F_1\}$, $\{W_2,F_2\}$, and $\{W_3,F_3\}$) can be determined using the following example. Whether, for the image pair 1, the pixel location (2,3) corresponds to a water-dominant location can be determined based on the two values of the pixel pair $W_1(2,3)$ and $F_1(2,3)$. For example, when the value of the pixel $W_1(2,3)$ is larger than the value of the pixel $F_1(2,3)$, the pixel location (2,3) is determined to be water-dominant for the first image pair. Alternatively, when the value of the pixel $W_1(2,3)$ is smaller than the value of the pixel $F_1(2,3)$, then the pixel location (2,3) is determined to be fat-dominant. In the case of a tie, a rule can be chosen to break the tie. For example, when the value of the pixel $W_1(2,3)$ is equal to the value of the pixel $F_1(2,3)$, the pixel $W_1(2,3)$ is determined to water-dominant. Alternatively, the rule for a tie can be that when the value of the pixel $W_1(2,3)$ is equal to the value of the pixel $F_1(2,3)$, the pixel $W_1(2,3)$ is determined to be fat-dominant.

Similarly, whether the pixel $W_2(2,3)$ in the water image 2 is water-dominant and whether the pixel $F_2(2,3)$ in the fat image 2 is fat-dominant can be determined based on the two values of the pixel pair $W_2(2,3)$ and $F_2(2,3)$. Further, whether the pixel $W_3(2,3)$ in the water image 3 is water-dominant and whether the pixel $F_3(2,3)$ in the fat image 3 is fat-dominant can be determined based on the two values of the pixel pair $W_3(2,3)$ and $F_3(2,3)$.

The majority of the pixels is water-dominant when most of the water images are determined to be water-dominant at pixel location (2,3). That is, whether the majority of the pixels is water-dominant or not can be determined by comparing a number of the pixels that is determined to water-dominant with a threshold of 50% of a number of the pixels used to determine the pixel location (2,3). When the number is larger than the threshold, the majority of the pixels is water-dominant. Otherwise, the majority of the pixels is not water-dominant, and thus, the majority of the pixels is determined to be fat-dominant.

In an example, the pixels $W_1(2,3)$ and $W_3(2,3)$ are determined to be water-dominant, the pixel $W_2(2,3)$ is determined not water-dominant, and the 50% threshold is 1.5 since 3 pixels $W_1(2,3)$, $W_2(2,3)$, and $W_3(2,3)$ are available at the pixel location (2,3). Therefore, the majority of the pixels $W_1(2,3)$, $W_2(2,3)$, and $W_3(2,3)$ is determined to be water-dominant, and the majority includes the pixels $W_1(2,3)$ and $W_3(2,3)$. Accordingly, the pixel W(2,3) in the initial combined water image 195B is determined to be water-dominant. The value of W(2,3) is then generated by combining the values of pixels $W_1(2,3)$ and $W_3(2,3)$, and the value of F(2,3) is then generated by combining the values of pixels $F_1(2,3)$ and $F_3(2,3)$. In one example, the values of the pixels in the majority are combined by averaging the values.

In another example, the pixels $W_1(2,3)$ and $W_3(2,3)$ are determined not water-dominant and the pixel $W_2(2,3)$ is determined to be water-dominant. Therefore, the majority of the pixels $W_1(2,3)$, $W_2(2,3)$, and $W_3(2,3)$ is determined not water-dominant, and the majority includes the pixels $W_1(2,3)$ and $W_3(2,3)$. Similarly, the pixel $W(2,3)$ is determined not water-dominant. Accordingly, the pixel $F(2,3)$ in the initial combined fat image 195C is determined to be fat-dominant. The value of $W(2,3)$ is then generated by combining the values of pixels $W_1(2,3)$ and $W_3(2,3)$, and the value of $F(2,3)$ is then generated by combining the values of pixels $F_1(2,3)$ and $F_3(2,3)$.

Accordingly, the value of the pixel $W(2,3)$ is calculated based on values of the majority of the pixels, i.e., $W_1(2,3)$ and $W_3(2,3)$. For example, the value of the pixel $W(2,3)$ is an average of the values of the pixels $W_1(2,3)$ and $W_3(2,3)$. Similarly, a value of a pixel $F(2,3)$ at the same location in the initial combined fat image 195C can be determined based on values of the pixels $F_1(2,3)$ and $F_3(2,3)$. In addition, a value of a pixel at the same location in the initial combined B0 field map 195A can be determined based on values of pixels at the same location in the B0 field maps 1 and 3.

In the description above, an odd number of pixels, such as $W_1(2,3)$, $W_2(2,3)$, and $W_3(2,3)$ is used to determine whether the majority of the pixels is water-dominant, and the majority of the pixels can include more than half of the pixels, such as $W_1(2,3)$ and $W_3(2,3)$.

At S186, chemical species separation is performed based on the initial set of combined images from S185 and the at least three MR images obtained at S182. Accordingly, a final set of combined images is obtained where the signals from the multiple chemical species are separated. The final set of combined images can include at least one of a final combined first image representing the first signal of the first species and a final combined second image representing the second signal of the second species. The final set of combined images can also include a final combined B0 field map and a T2* map where T2* is an effective transverse relaxation time including effects of the multiple chemical species.

Referring to FIG. 1B, the final set of combined images 196 can include a final combined B0 field map 196A, a final combined water image 196B, a final combined fat image 196C, and a T2* map 196D where the effective transverse relaxation time T2* includes effects of water and fat. The final combined B0 field map 196A, the final combined water image 196B, the final combined fat image 196C, and the T2* map 196D can be obtained using any suitable methods, such as a pixel-wise nonlinear fitting method based on initial set of combined images 195 and the at least three MR images 192. In an example, when the final set of combined images 196 includes 3D images, pixel-wise nonlinear fitting methods are referred to as voxel-wise nonlinear fitting methods. The method 180 proceeds to S189, and terminates.

The final combined water image 196B is a water-only image that indicates the water signal of the tissue, and the final combined fat image 196C is a fat-only image that indicates the fat signal of the tissue. Therefore, the water signal and the fat signal are separated into different images.

Referring to FIG. 1B, two echo times are associated with each dual-echo pair, for example, the two echo times TE1 and TE2 are associated with the dual-echo pair 193(1). Certain combinations of the two echo times can lead to inaccurate estimation of a B0 field map and thus, an inaccurate separation of the multiple chemical species, such as water and fat, resulting in a water-fat swap and consequently a pixel that is water-dominant is determined to be fat-dominant or vice versa. Therefore, according to aspects of the disclosure, instead of using a water image and a fat image estimated from a single dual-echo pair, multiple water images and fat images estimated from a plurality of dual-echo pair are used to better separate the multiple chemical species, as described above.

Referring to FIGS. 1A and 1B, multiple steps are used to separate the signals of the multiple chemical species. For example, in the step S184, the signals are separated for each dual-echo pair to form the separate water and fat images, such as the water image 1 and the fat image 1 for the dual-echo pair 193(1). In the step S185, the initial combined water image 195B and the initial combined fat image 195C that are associated with the plurality of dual-echo pairs are generated based on the water images and the fat images obtained from individual dual-echo pairs. Accordingly, the initial combined water image 195B and the initial combined fat image 195C can be more accurate than certain water image and fat image estimated from a single dual-echo pair. In the example shown in FIG. 1C, water-fat swap occurs for certain pixels in the water image 2 and fat image 2 (e.g., the pixels located at (2,3)), which are estimated from the single dual-echo pair 193(2), providing an inaccurate result. However, corresponding pixels in the additional dual-echo pairs 193(1) and 193(3) that are not water-fat swapped can be used together with the certain pixels in the water image 2 and fat image 2, providing an accurate result. Accordingly, the pixels $W(2,3)$ and $F(2,3)$ in the initial combined water and fat images 195B-195C, respectively, are not water-swapped and provide an accurate result. Similarly, the initial combined B0 field map 195A can be more accurate than the B0 field maps i obtained from the single dual-echo pair 193(i).

In the step S186, the final set of combined images are generated based on the initial set of combined images and the at least three MR images. The final set of combined images can be more accurate when the initial set of combined images is more accurate.

In a related method, instead of using the steps S183-S185, an initial set of combined images can also be obtained by jointly processing the at least three MR images, such as all six MR images 192(1)-(6) where a difference phase $\Delta\varphi$ is assumed to evolve linearly with the echo times TE1-TE6, respectively. However, in various examples, the difference phase $\Delta\varphi$ does not evolve linearly with the echo times TE1-TE6, and thus, the above assumption can also result in inaccurate chemical species separation such as water-fat swap and an inaccurate estimation of a B0 field map. In the steps S184-S185 described above, two MR images in each dual-echo pair are processed together, and the difference phase $\Delta\varphi$ is not assumed to evolve linearly with the echo times, and thus, can lead to more accurate chemical species separation. Accordingly, the methods described herein can be more accurate and robust than the related method that jointly processes the at least three MR images by assuming a linear relationship between the difference phase $\Delta\varphi$ and the echo times and without performing dual-echo separation on respective pairs of the at least three MR images, as described herein.

Figure 2A:
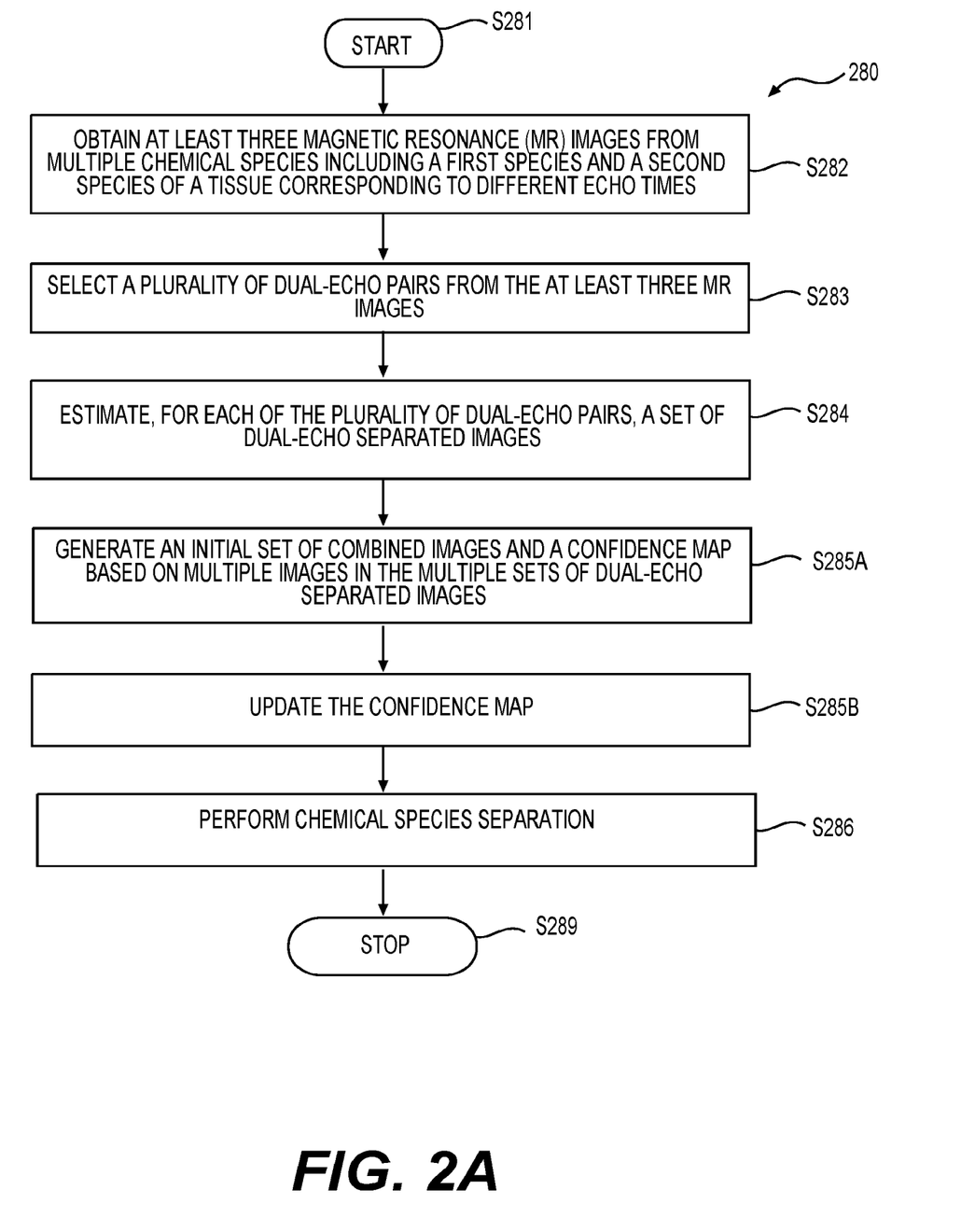
FIG. 2A shows an example of a method 280 to perform chemical species separation according to an embodiment of the disclosure.
Figure 2B:
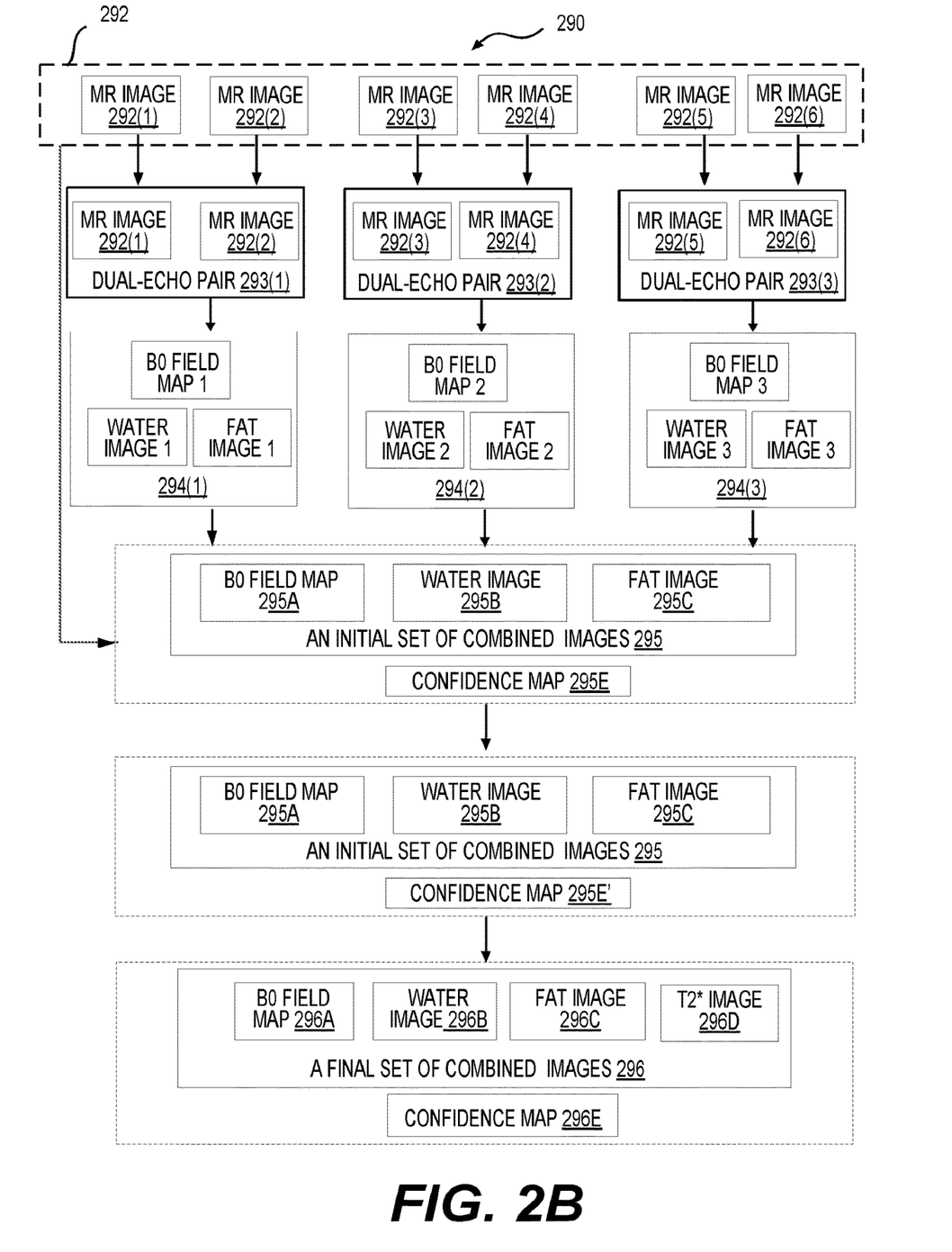
FIG. 2B shows an example 290 corresponding to the method 280 according to an embodiment of the disclosure.

FIG. 2A shows an example of a method 280 to perform chemical species separation according to an embodiment of the disclosure. FIG. 2B shows an example 290 corresponding to the method 280 according to an embodiment of the disclosure. The method 280 includes similar steps as those of the method 180 described in FIG. 1A. A reference numeral 2xx in FIG. 2A designates an identical or a similar step as that of a reference numeral 1xx in FIG. 1A where xx is a number from 81 to 84, and thus, the detailed description of the steps in FIG. 2A that are identical to those in FIG. 1A is omitted for purposes of brevity. The example 290 includes similar parts as those of the example 190 described in FIG. 1B. The method 280 starts at S281, and proceeds to S282.

At S282, at least three MR images corresponding to different echo times are obtained from a tissue. Similar to the above description, the tissue has multiple chemical species including a first species, a second species, and the like. Each of the at least three MR images represents signals from the multiple chemical species, and the signals includes a first signal of the first species, a second signal of the second species, and the like. In various examples of MRI, such as the example 290 in FIG. 1B, water and fat are major contributors to the signals where the first species is water and the second species is fat, and thus, the first signal is a water signal and the second signal is a fat signal.

Referring to FIG. 2B, the at least three MR images 292 in the example 290 can be acquired using the MRI system shown in FIG. 3. The at least three MR images 292 includes six MR images 292(1)-(6) acquired at six different TEs, TE1 to TE6, respectively, respect to a time t0. The tissue includes water and fat. The six MR images 292(1)-(6) are identical or similar to the six MR images 192(1)-(6) in FIG. 1B, and thus the detailed description of the six MR images 292(1)-(6) is omitted for purposes of brevity.

At S283, a plurality of dual-echo pairs can be selected from the at least three MR images. Referring to the example 290 in FIG. 2B, the plurality of dual-echo pairs includes three dual-echo pairs 293(1)-(3) that are identical or similar to the three dual-echo pairs 193(1)-(3) in FIG. 1B, and thus the detailed description of the three dual-echo pairs 293(1)-(3) is omitted for purposes of brevity.

At S284, for each pair of the plurality of dual-echo pairs, a set of images (or a set of dual-echo separated images) is estimated and the signals of the multiple chemical species are separated in the set of images. The set of images can be similar or identical to that described in FIG. 1B. Referring to the example 290 in FIG. 2B, for the dual-echo pair 293($i$), the set of images 294($i$) can include a B0 field map i, a water image i, and a fat image i where i is an integer and $1 \leq i \leq 3$. The set of images 294($i$) including the B0 field map i, the water image i, and the fat image i is identical or similar to the set of images 194($i$) in FIG. 1B, and thus the detailed description is omitted for purposes of brevity.

At S285A, an initial set of combined images is generated based on multiple images in the multiple sets of images for the plurality of dual-echo pairs and the signals of the multiple chemical species are separated in the initial set of combined images. S285A can include an identical or similar implementation as that described in the step S185, and thus, the detailed description of the implementation of S285A that is identical or similar to that in FIG. 1A is omitted for purposes of brevity. Referring to FIG. 2B, the initial set of combined images 295 can include an initial combined B0 field map 295A, an initial combined water image 295B, and an initial combined fat image 295C. The initial set of combined images 295 is identical or similar to the initial set of combined images 195 in FIG. 1B, and thus, the detailed description of initial set of combined images 295 is omitted for purposes of clarity.

Figure 2C:
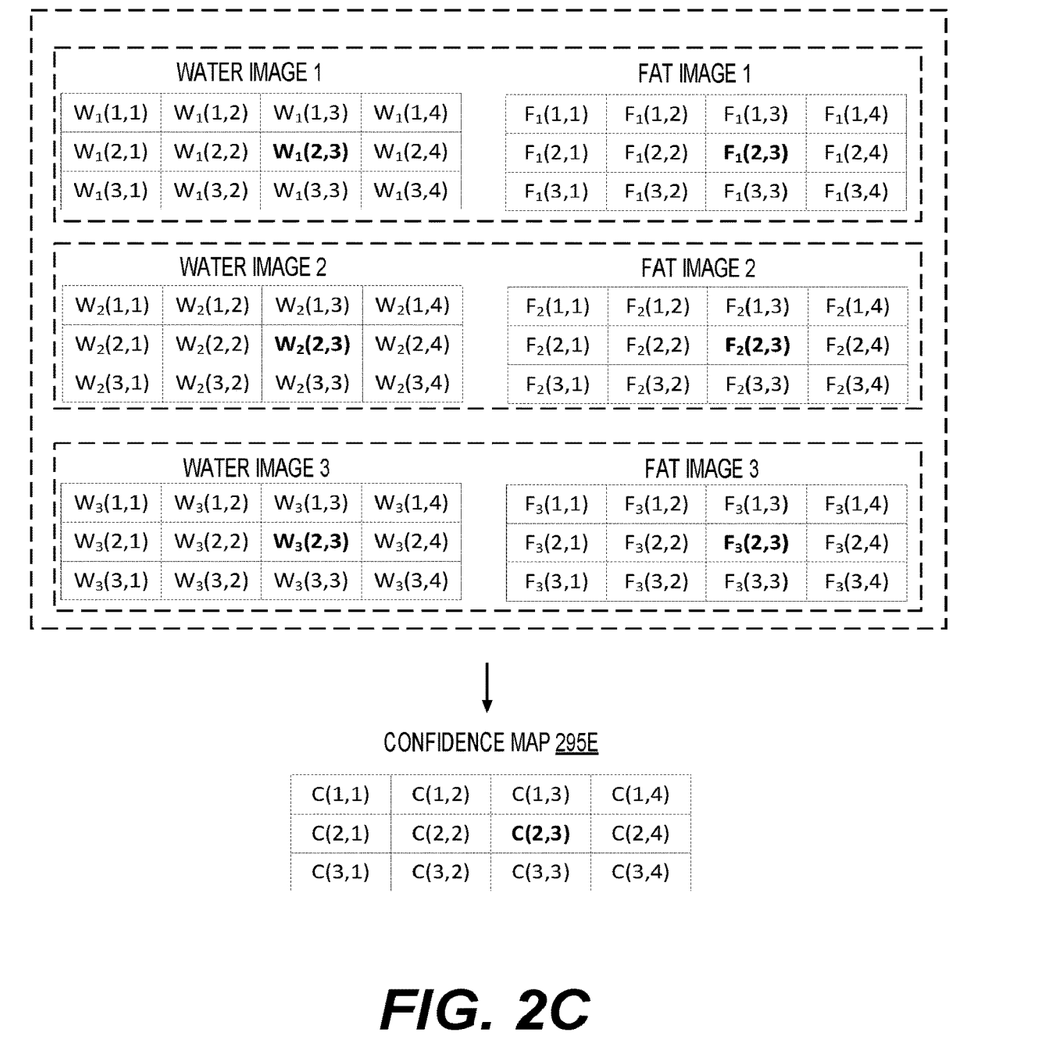
FIG. 2C shows an example to generate a confidence map according to an embodiment of the disclosure.

At S285A, a confidence map can further be determined, for example, based on multiple images in the multiple sets of images for the plurality of dual-echo pairs. Referring to FIGS. 2B-2C, the confidence map 295E can be determined based on the multiple images including the water images 1-3 and the fat images 1-3. A value (or a confidence value) in a pixel of the confidence map 295E can indicate confidence levels (or degrees of reliability) of the respective pixels in the B0 field map 295A, the water image 295B, and the fat image 295C.

The confidence map 295E can represent a size of the majority in the voting method. On the one hand, if only two out of the three pixels are in agreement with regards to whether a given pixel location is fat- or water-dominant, then the confidence value is 2/3. On the other hand, if only three out of the three pixels are in agreement with regards to whether a given pixel location is fat- or water-dominant, then the confidence value is 1. In the case of five images rather than the three images, a range of confidence values can be 3/5, 4/5, and 1, corresponding to majorities of three out of five, four out of five, and five out of five, respectively.

The water images 1-3 and the fat images 1-3 in FIG. 2C can be identical to the water images 1-3 and the fat images 1-3 in FIG. 1C. Similarly, the confidence map 295E is a 3×4 2D image. A voting method can be used to generate the confidence map 295E. In an embodiment, to determine a value of a pixel at a location in the tissue, such as a pixel C(2,3) in the confidence map 295E, corresponding values of pixels in the water images 1-3 and the fat images 1-3 at the same location are used.

In the voting method of FIG. 2C, whether a majority of the pixels is water-dominant or fat-dominant can be determined similarly as that described with reference to FIG. 1C. In an first example, the pixels $W_1(2,3)$, $W_2(2,3)$, and $W_3(2,3)$ at the same location can be used to determine the pixel C(2,3). The pixels W1(2,3) and W3(2,3) are determined to be water-dominant, the pixel W2(2,3) is determined not water-dominant, and a first threshold is 1.5. In the example, a first number of the pixels $W_1(2,3)$, $W_2(2,3)$, and $W_3(2,3)$ used to determine the pixel C(2,3) is 3 and a second number of the pixels W1(2,3) and W3(2,3) being the majority of the pixels and determined to be water-dominant is 2. Therefore, the pixel W(2,3) in the initial combined water image 295B is determined to be water-dominant, and the pixel F(2,3) in the initial combined fat image 295C is determined not fat-dominant. Further, a value of the pixel C(2,3) can be determined to be a ratio of the second number over the first number, i.e., 2/3.

In a second example, the pixels W1(2,3) and W3(2,3) are determined not water-dominant and the pixel W2(2,3) is determined to be water-dominant. Accordingly, the pixels F1(2,3) and F3(2,3) are determined to be fat-dominant and the pixel F2(2,3) is determined not fat-dominant. Therefore, the pixel F(2,3) in the initial combined fat image 295C is determined to be fat-dominant. Similarly, the second number of the pixels being the majority of the pixels determined to be fat-dominant is 2. The first number of the pixels used to determine the pixel C(2,3) is 3, and thus, a value of the pixel C(2,3) can be determined to be a ratio of the second number over the first number, i.e., 2/3.

In the above examples, the value of the pixel C(2,3) is 2/3. In the first example, the value of the pixel C(2,3) indicates a confidence level of the pixel location (2,3) being dominated by water. In the second example, the value of the pixel C(2,3) indicates a confidence level of the pixel location (2,3) being dominated by fat.

In a third example, the pixels $W_1(3,3)$, $W_2(3,3)$, and $W_3(3,3)$ can be used to determine the pixel C(3,3), and the pixels $W_1(3,3)$, $W_2(3,3)$, and $W_3(3,3)$ are determined to be water-dominant. Therefore, the pixel W(3,3) in the initial combined water image 295B is determined to be water-dominant, and thus the value of the pixel C(3,3) can be determined to be 1 (i.e., 3/3). In an example, based on the values of the pixels C(2,3) and C(3,3), the pixel W(3,3) is more likely to be truly water-dominant than the pixel W(2,3) though both the pixels W(2,3) and W(3,3) are determined to be water-dominant.

In an embodiment, if an even number of water images and an even number of fat images are used, a rule can be defined for breaking ties. For example, when half of the pixels are water-dominant, the corresponding pixel in the initial combined water image can be determined to be dominated by water, and thus the value of the pixel in the confidence map can be determined to be 0.5.

At S285B, the confidence map can further be updated. In an embodiment, a value of a pixel in the confidence map that is relatively low can be increased based on values of neighboring pixels of the pixel in the confidence map.

Figure 2D:
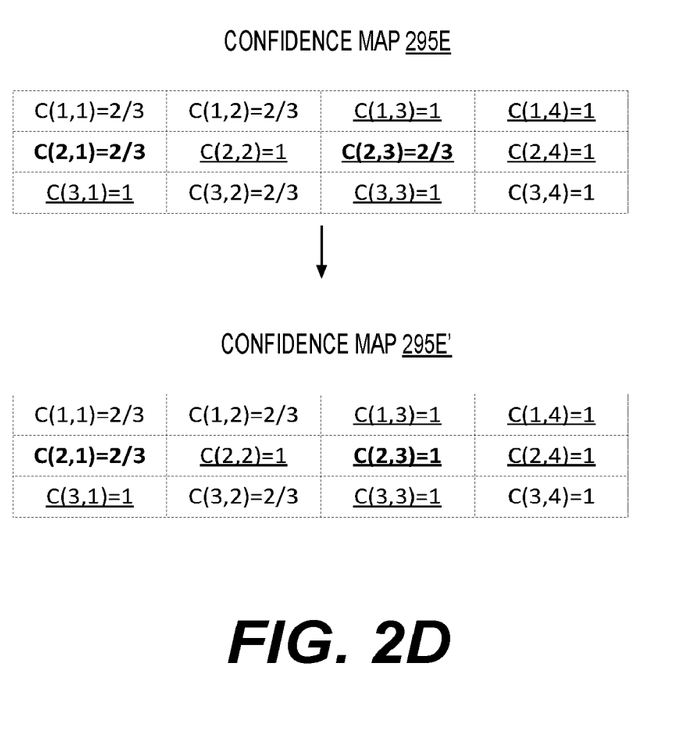
FIG. 2D shows an example to update the confidence map according to an embodiment of the disclosure.

Referring to FIGS. 2B and 2D, the confidence map 295E can be updated to result in an updated confidence map 295E'. In an embodiment, whether a value of a pixel in the confidence map 295E is large can be determined, for example, by comparing the value of the pixel with a confidence threshold, such as 4/5. When the value of the pixel is larger than the confidence threshold, the value of the pixel is determined to be large and is not updated. Accordingly, the same value is used in a corresponding pixel of the updated confidence map 295E'. Otherwise, when the value of the pixel is equal to or less than the confidence threshold, the value of the pixel is determined to be low. Referring to FIG. 2D, values of pixels in the confidence map 295E are shown in the respective pixels. Pixels underlined in the confidence map 295E and the updated confidence map 295E' correspond to pixels that are determined to be dominated by water. Remaining pixels in the confidence map 295E and the updated confidence map 295E' correspond to pixels that are determined to be dominated by fat. A value of a pixel C(1,3) in the confidence map 295E is 1, and thus the value is determined to be large and the same value (i.e., 1) is used in a corresponding pixel C'(1,3) of the updated confidence map 295E'. On the other hand, a value of a pixel C(2,3) in the confidence map 295E is 2/3, and thus the value of the pixel C(2,3) is determined to be low.

When the value of the pixel C(2,3) is determined to be low, neighboring pixels of the pixel C(2,3) can be determined. The neighboring pixels can include any suitable pixels that are spatially close to the pixel C(2,3). The neighboring pixels can include one or more pixels that are adjacent to the pixel C(2,3) and/or one or more pixels that are not adjacent to the pixel C(2,3). In an embodiment, the neighboring pixels can include pixels that are dominated by water and fat. In an embodiment, the neighboring pixels can include pixels that are dominated by one of: water and fat. In an embodiment, when the pixel W(2,3) in the initial combined water image 295B is dominated by water, pixels in the initial combined water image 295B corresponding to the neighboring pixels are also dominated by water. In an example, pixels C(1,2), C(1,3), C(1,4), C(2,2), C(2,4), C(3,2), C(3,3), and C(3,4) are adjacent to the pixel C(2,3), pixels W(1,3), W(1,4), W(2,2), W(2,4), and W(3,3) in the initial combined water image 295B corresponding to the pixels C(1,3), C(1,4), C(2,2), C(2,4), and C(3,3) are determined to be dominated by water, and pixels W(1,2), W(3,2), and W(3,4) in the initial combined water image 295B corresponding to the pixels C(1,2), C(3,2), and C(3,4) are determined not to be dominated by water. Accordingly, in an example, the neighboring pixels of the pixel C(2,3) include the pixels C(1,3), C(1,4), C(2,2), C(2,4), and C(3,3), and do not include the pixels C(1,2), C(3,2), and C(3,4). Any suitable methods and/or criteria can be used to determine whether the values of the neighboring pixels of the pixel C(2,3) can be used to update the pixel C(2,3). In an example, an average of the values of the neighboring pixels is determined and compared with the value of the pixel C(2,3). When the averaged value of the neighboring pixels is larger than the second confidence threshold, the corresponding pixel C'(2,3) in the updated confidence map 295E' can be determined based on the values of the neighboring pixels, such as the averaged value. Referring to FIG. 2D, the averaged value is 1, and thus, the value of the corresponding pixel C'(2,3) is determined to be 1. The value of the pixel C'(2,3) is increased from 2/3, i.e., the value of the pixel C(2,3).

In another example, a value of the pixel C(2,1) is 2/3 and a corresponding pixel F(2,1) in the initial combined fat image 295C is dominated by fat. Pixels C(1,1), C(1,2), C(2,2), C(3,1), and C(3,2) are adjacent to the pixel C(2,1), pixels W(2,2) and W(3,1) in the initial combined water image 295B corresponding to the pixels C(2,2) and C(3,1) are determined to be water-dominant, and pixels F(1,1), F(1,2), and F(3,2) in the initial combined fat image 295C corresponding to the pixels C(1,1), C(1,2), and C(3,2) are determined to be fat-dominant. Accordingly, in an example, the neighboring pixels of the pixel C(2,1) include the pixels C(1,1), C(1,2), and C(3,2), and do not include the pixels C(2,2) and C(3,1). An averaged value of the neighboring pixels C(1,1), C(1,2), and C(3,2) of the pixel C(2,1) is 2/3, and thus, the averaged value is not larger than the value of the pixel C(2,1) (i.e., 3/5). Therefore, the pixel C(2,1) is not updated and remains the same in the updated confidence map 295E'.

In some examples, an averaged value of the neighboring pixels can be less than or equal to the value of the pixel in the confidence map 295E, and thus, the value of the pixel in the confidence map 295E remains the same.

The above description can be applied to each pixel in the confidence map 295E and can generate the updated confidence map 295E'. The above description can also be suitably adapted.

At S286, chemical species separation is performed based on the initial set of combined images from S285A and the at least three MR images obtained at S282. Accordingly, a final set of combined images is obtained where the signals from the multiple chemical species are separated. The final set of combined images can include at least one of a final combined first image representing the first signal of the first species and a final combined second image representing the second signal of the second species. The final set of combined images can also include a final combined B0 field map and a T2* map where T2* is an effective transverse relaxation time including effects of the multiple chemical species.

Referring to FIG. 2B, the final set of combined images 296 can include a final combined B0 field map 296A, a final combined water image 296B, a final combined fat image 296C, and a T2* map 296D where the effective transverse relaxation time T2* includes effects of water and fat. The final set of combined images 296 can be obtained similarly as described above in FIG. 1B and S186.

In an example, a confidence map 296E is identical to the updated confidence map 295E'. In an example, the confidence map 296E can be obtained based on the updated confidence map 295E' and the final set of combined images 296, such as the final combined water image 296B and the final combined fat image 296C.

The final combined water image 296B is a water-only image that indicates the water signal of the tissue, and the final combined fat image 296C is a fat-only image that indicates the fat signal of the tissue. Therefore, the water signal and the fat signal are separated into different images. Further, the confidence map 296E indicates a confidence level of each of the final set of combined images 296. In some examples, the confidence map 296E can be displayed over each of the final set of combined images 296 to indicate confidence levels of corresponding voxels. The method 280 proceeds to S289, and terminates.

FIG. 3 shows a non-limiting example of the MRI system 100. The MRI system 100 depicted in FIG. 3 includes a gantry 101 (shown in a schematic cross-section) and various related system components 103 interfaced therewith. At least the gantry 101 is typically located in a shielded room. The MRI system geometry depicted in FIG. 3 includes a substantially coaxial cylindrical arrangement of the static field magnet 111, a Gx, Gy, and Gz gradient coil set 113, and a large whole-body RF coil (WBC) assembly 115. Along a horizontal axis of this cylindrical array of elements is an imaging volume 117 shown as substantially encompassing the head of a patient 119 supported by a patient table 120.

One or more smaller array RF coils 121 can be more closely coupled to the patient's head (referred to herein, for example, as "scanned object" or "object") in imaging volume 117. As those in the art will appreciate, compared to the WBC (whole-body coil), relatively small coils and/or arrays, such as surface coils or the like, are often customized for particular body parts (e.g., arms, shoulders, elbows, wrists, knees, legs, chest, spine, etc.). Such smaller RF coils are referred to herein as array coils (AC) or phased-array coils (PAC). These can include at least one coil configured to transmit RF signals into the imaging volume, and a plurality of receiver coils configured to receive RF signals from an object, such as the patient's head, in the imaging volume.

The MRI system 100 includes a MRI system controller 130 that has input/output ports connected to a display 124, a keyboard 126, and a printer 128. As will be appreciated, the display 124 can be of the touch-screen variety so that it provides control inputs as well. A mouse or other I/O device(s) can also be provided.

The MRI system controller 130 interfaces with a MRI sequence controller 140, which, in turn, controls the Gx, Gy, and Gz gradient coil drivers 132, as well as the RF transmitter 134, and the transmit/receive switch 136 (if the same RF coil is used for both transmission and reception). The MRI sequence controller 140 includes suitable program code structure 138 for implementing MRI imaging (also known as nuclear magnetic resonance, or NMR, imaging) techniques including parallel imaging. The MRI sequence controller 140 can be configured for MR imaging with or without parallel imaging. Moreover, the MRI sequence controller 140 can facilitate one or more preparation scan (pre-scan) sequences, and a scan sequence to obtain a main scan MR image (referred to as a diagnostic image). MR data from pre-scans can be used, for example, to determine sensitivity maps for RF coils 115 and/or 121 (sometimes referred to as coil sensitivity maps or spatial sensitivity maps), and to determine unfolding maps for parallel imaging.

The MRI system components 103 include an RF receiver 141 providing input to data processor 142 so as to create processed image data, which is sent to display 124. The MRI data processor 142 is also configured to access previously generated MR data, images, and/or maps, such as, for example, coil sensitivity maps, parallel image unfolding maps, distortion maps and/or system configuration parameters 146, and MRI image reconstruction program code structures 144 and 150.

In one embodiment, the MRI data processor 142 includes processing circuitry. The processing circuitry can include devices such as an application-specific integrated circuit (ASIC), configurable logic devices (e.g., simple programmable logic devices (SPLDs), complex programmable logic devices (CPLDs), and field programmable gate arrays (FPGAs), and other circuit components that are arranged to perform the functions recited in the present disclosure. In an example, the processing circuitry of the MRI data processor 142 is configured to perform various steps in the method 180 and the method 280.

The MRI data processor 142 executes one or more sequences of one or more instructions contained in the program code structures 144 and 150. Alternatively, the instructions can be read from another computer-readable medium, such as a hard disk or a removable media drive. One or more processors in a multi-processing arrangement can also be employed to execute the sequences of instructions contained in the program code structures 144 and 150. In alternative embodiments, hard-wired circuitry can be used in place of or in combination with software instructions. Thus, the disclosed embodiments are not limited to any specific combination of hardware circuitry and software. In an example, instructions for performing chemical species separation, such as described with reference to the method 180 and the method 280, can be stored in the program code structures 144 and/or 150.

Additionally, the term "computer-readable medium" as used herein refers to any non-transitory medium that participates in providing instructions to the MRI data processor 142 for execution. A computer readable medium can take many forms, including, but not limited to, non-volatile media or volatile media. Non-volatile media includes, for example, optical, magnetic disks, and magneto-optical disks, or a removable media drive. Volatile media includes dynamic memory.

Also illustrated in FIG. 3 is a generalized depiction of an MRI system program storage (memory) 150, where stored program code structures are stored in non-transitory computer-readable storage media accessible to the various data processing components of the MRI system 100. As those in the art will appreciate, the program store 150 can be segmented and directly connected, at least in part, to different ones of the system 103 processing computers having most immediate need for such stored program code structures in their normal operation (i.e., rather than being commonly stored and connected directly to the MRI system controller 130).

Additionally, the MRI system 100 as depicted in FIG. 3 can be utilized to practice exemplary embodiments described herein below. The system components can be divided into different logical collections of "boxes" and typically comprise numerous digital signal processors (DSP), microprocessors and special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Furthermore, not only does the physical state of the processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an image reconstruction process and/or sometimes an image reconstruction map (e.g., coil sensitivity map, unfolding map, ghosting map, a distortion map etc.) generation process, an array of computer-readable accessible data value storage sites in physical storage media will be transformed from some prior state to a new state wherein the physical states at the physical sites of such an array vary between minimum and maximum values to represent real world physical events and conditions. As those in the art will appreciate, such arrays of stored data values represent and also constitute a physical structure, as does a particular structure of computer control program codes that, when sequentially loaded into instruction registers and executed by one or more CPUs of the MRI system 100, causes a particular sequence of operational states to occur and be transitioned through within the MRI system 100.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. A method, comprising:
   obtaining at least three magnetic resonance (MR) images corresponding respectively to different echo times, the at least three MR images representing signals from multiple chemical species including a first species and a second species in a tissue;
   selecting, from the at least three MR images, a plurality of dual-echo pairs;
   estimating, for each pair of the plurality of dual-echo pairs, a set of dual-echo separated images including a B0 field map indicating spatial inhomogeneity of magnetic field strength in the tissue, a first image representing a first signal of the first species, and a second image representing a second signal of the second species; and
   generating an initial set of combined images including one or more of: (i) an initial combined B0 field map formed by combining two or more of the B0 field maps, (ii) an initial combined first image formed by combining two or more of the first images and (iii) an initial combined second image formed by combining two or more of the second images.

2. The method according to claim 1, wherein generating the initial set of combined images comprises:
   generating the initial set of combined images that includes the initial combined first image and the initial combined second image by:
   combining the two or more of the first images to generate the initial combined first image; and
   combining the two or more of the second images to generate the initial combined second image.

3. The method according to claim 2, further comprising:
   performing, based on the initial set of combined images and the at least three MR images, chemical species separation by generating a final set of combined images including at least a final combined first image.

4. The method according to claim 3, wherein performing the chemical species separation comprises:
   implementing a pixel-wise nonlinear fitting method to obtain the final set of combined images, the final set of combined images further comprising a final combined B0 field map, a final combined second image, and a T2* map indicating an effective transverse relaxation time T2* of the multiple chemical species in the tissue.

5. The method according to claim 1, wherein estimating the set of dual-echo separated images is implemented using a dual-echo separation technique.

6. The method according to claim 1, wherein estimating the set of dual-echo separated images includes that the first species is water and the second species is fat.

7. The method according to claim 2, wherein generating the initial set of combined images comprises:
   for each pixel location in the tissue,
   identifying, for each pair of the plurality of dual-echo pairs, which of the first species and second species is a dominant species at the pixel location:
   identifying, at the pixel location, a majority dominant species that is the dominant species for a majority of the plurality of dual-echo pairs; and
   determining, at the pixel location, a pixel value of the initial combined first image by combining the pixel values of the first images for which the dominant species is a same species as the majority dominant species.

8. The method according to claim 7, further comprising:
   generating a confidence map representing a degree of reliability for values of the initial combined first image at each of the pixel locations based on a size of the majority of the plurality of dual-echo pairs corresponding to the majority dominant species at the pixel location.

9. The method according to claim 8, further comprising updating a value of a pixel in the confidence map based on values of neighboring pixels in the confidence map.

10. The method according to claim 8, wherein generating the confidence map is performed using a voting method and a number of the plurality of dual-echo pairs being an odd integer larger than 2.

11. An apparatus, comprising processing circuitry configured to:
    obtain at least three magnetic resonance (MR) images corresponding respectively to different echo times, the at least three MR images representing signals from multiple chemical species including a first species and a second species in a tissue;
    select, from the at least three MR images, a plurality of dual-echo pairs;
    estimate, for each pair of the plurality of dual-echo pairs, a set of dual-echo separated images including a B0 field map indicating spatial inhomogeneity of magnetic field strength in the tissue, a first image representing a first signal of the first species, and a second image representing a second signal of the second species; and
    generate an initial set of combined images including one or more of: (i) an initial combined B0 field map formed by combining two or more of the B0 field maps, (ii) an initial combined first image formed by combining two or more of the first images, and (iii) an initial combined second image formed by combining two or more of the second images.

12. The apparatus according to claim 11, wherein the processing circuitry is further configured to:
    generate the initial set of combined images that includes the initial combined first image and the initial combined second image by:
    combining the two or more of the first images to generate the initial combined first image; and combining the two or more of the second images to generate the initial combined second image.

13. The apparatus according to claim 12, wherein the processing circuitry is further configured to:

perform, based on the initial set of combined images and the at least three MR images, chemical species separation by generating a final set of combined images including at least a final combined first image.

14. The apparatus according to claim 13, wherein the processing circuitry is further configured to:

implement a pixel-wise nonlinear fitting method to obtain the final set of combined images, the final set of combined images further comprising a final combined B0 field map, a final combined second image, and a T2* map indicating an effective transverse relaxation time T2* of the multiple chemical species in the tissue.

15. The apparatus according to claim 11, wherein the processing circuitry is further configured to implement a dual-echo separation technique to estimate the set of dual-echo separated images.

16. The apparatus according to claim 11, wherein the processing circuitry is configured to estimate the set of dual-echo separated images when the first species is water and the second species is fat.

17. The apparatus according to claim 12, wherein the processing circuitry is further configured to:

for each pixel location in the tissue,
identify, for each pair of the plurality of dual-echo pairs, which of the first species and second species is a dominant species at the pixel location;
identify, at the pixel location, a majority dominant species that is the dominant species for a majority of the plurality of dual-echo pairs; and
determine, at the pixel location, a pixel value of the initial combined first image by combining the pixel values of the first images for which the dominant species is a same species as the majority dominant species.

18. The apparatus according to claim 17, wherein the processing circuitry is configured to:

generate a confidence map representing a degree of reliability for values of the initial combined first image at each of the pixel locations based on a size of the majority of the plurality of dual-echo pairs corresponding to the majority dominant species at the pixel location.

19. The apparatus according to claim 18, wherein the processing circuitry is further configured to:

update a value of a pixel in the confidence map based on values of neighboring pixels in the confidence map.

20. The apparatus according to claim 18, wherein the processing circuitry is configured to:

generate the confidence map by using a voting method when a number of the plurality of dual-echo pairs is an odd integer larger than 2.

* * * * *